US00PP33540P2

(12) United States Plant Patent
Clark

(10) Patent No.: US PP33,540 P2
(45) Date of Patent: Oct. 5, 2021

(54) COLEUS PLANT NAMED 'UF15-11-3'

(50) Latin Name: *Plectranthus scutellarioides*
Varietal Denomination: UF15-11-3

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/974,429

(22) Filed: Jan. 30, 2021

(51) Int. Cl.
*A01H 5/12* (2018.01)
*A01H 6/50* (2018.01)

(52) U.S. Cl.
USPC ..... Plt./469
CPC ..... *A01H 6/50* (2018.05)

(58) Field of Classification Search
USPC ..... Plt./469, 373
CPC ..... A01H 5/00; A01H 5/12
See application file for complete search history.

(56) References Cited

PUBLICATIONS http://www.ffsp.net/wp-content/uploads/2020/12/ITN20-07-11.pdf; Dec. 11, 2020; 8 pages.*

* cited by examiner

*Primary Examiner* — Kent L Bell
(74) *Attorney, Agent, or Firm* — Katherine Koenig; Koenig IP Works, PLLC

(57) ABSTRACT

A new and distinct cultivar of *Plectranthus scutellarioides* (coleus) named 'UF15-11-3', selected because it has a combination of desirable traits not often found in our program. It has orange and chartreuse foliage with superior stability in both sun and shade. The lanced shape of the foliage is extremely uniform across the plant throughout development. It has excellent lateral branching, thus providing ample vegetative propagules for producers. It has a vigorous spreading habit, growing more horizontal than vertical, which allows it to fill space with vibrant color very quickly in summer gardens. It has superior stability in foliage color in both sun and shade conditions, maintaining stable color in all conditions. 'UF15-11-3' has not been observed to produce flowers in any trial we have conducted to date, so it has long season performance as an annual plant in the landscape until late Fall.

3 Drawing Sheets

Genus and species: *Plectranthus scutellarioides*.

Cultivar denomination: The present disclosure relates to coleus cultivar 'UF15-11-3'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

Coleus (previously *Solenostemon scutellarioides*, now *Plectranthus scutellarioides*) plants are used as annual bedding plants for the landscape and mixed containers in summer gardens. Coleus plants are popular for commercial growers and landscapers because they are easy to propagate and provide fast and reliable attractive foliage color that performs well at all points in the perishable garden plant supply chain. Coleus plants are also popular with home gardeners because they are easy to grow in both full sun and partial shade conditions, and require less maintenance than many other annual garden plants. From the breeder perspective, there is much genotypic variability in coleus because it is a tetraploid with active transposons and there are a number of different visible phenotypes including foliage color, leaf shape and size, plant height, time to flowering, and growth habit.

The coleus breeding program in Gainesville, Fla., was initiated in 2003 with an emphasis on developing new clonally propagated cultivars that are profitable for producers and perform well in consumer gardens with little or no care. Using recurrent mass selection and maintaining a large pool of germplasm our program has released over 85 new cultivars into the industry since 2007. The coleus breeding program has focused on screening for new cultivars with novel leaf colors and shapes, increased vigor and branching, and late flowering, by conducting greenhouse and field trials under demanding environmental conditions. Greenhouse trials under "lush" conditions that push the plants to grow as fast as possible with high amounts of light, high fertility and high temperatures are used because these conditions allow for rapid discernment of growth habits and vigor characteristics, and also facilitate observation of plant phenotypes under conditions where greenhouse pathogen and insect pressure is highest. A first group of field trials in Citra, Fla., are planted in full sun in sand beds with plastic mulch in May-June each year with drip irrigation, minimal added fertilizer, and no chemical control for insects or pathogens. A second group of field trials in Citra, Fla., are planted in 30% shade in sand beds in May-June each year with drip irrigation and a minimal amount of slow-release fertilizer added at planting. These "lean" growing conditions are used in the field trials to screen for plants that grow vigorously and consistently for minimalist gardeners. Coleus produces a better seed crop under "lean" conditions than "lush" conditions, which is useful for making open-pollinated seeds. Since data is collected on a large number of genotypes (~600-800 per year), each trial only contains 1-3 plants per genotype. If a genotype performs poorly in any trial it is automatically discarded from the program, leaving ~200-250 genotypes in the program as elite stock at the end of each year.

Desirable characteristics that continue to be in demand a decade after first commercial introductions are: (1) foliage color stability in sun and shade; (2) consistent well-branched plant habit; and (3) late flowering. Improved plants with interesting foliage colors in both full sun and shade conditions allow for more versatile garden use and more color choices for gardeners. Superior well-branched plant habit is important throughout the production chain from the propagator/grower to the consumer, which allows for production of a large number of vegetative propagules and translates into more manageable plants for producers during culture and shipping to retail outlets. Once planted in the garden, these well-branched plants require less management over a long season of growth. Late flowering is a desirable characteristic because early flowering triggers senescence of the lower leaves and decreases foliage quality of coleus. Floral induction often slows vegetative growth, and increases landscape maintenance with manual dead-heading and plant replacement, which is vital to landscape contractors. Late or 'no flowering' genotypes with good branching and stable foliage color that have been developed in Gainesville, Fla., have performed well in commercial markets, and continue to attract interest from US, European, and Asian gardeners. The plant disclosed herein was selected because it has many of these desirable traits.

SUMMARY OF THE INVENTION

The invention relates to a new and distinct cultivar of coleus plant named 'UF15-11-3'. The new cultivar 'UF15-11-3' originated from an open pollination conducted in May-November 2014 in Gainesville, Fla., between the female coleus plant 'UF14-2-6' (unpatented) and an unknown male coleus plant. A single seedling was chosen in May 2015 for further asexual propagation in Gainesville, Fla. FIG. 1 shows the pedigree of 'UF15-11-3'.

The new cultivar 'UF15-11-3' has been reproduced asexually for over eighteen (18) months through vegetative cuttings and has been found to retain its distinctive characteristics through successive asexual propagations. 'UF15-11-3' was first propagated asexually by meristem tip cuttings in May 2015 in Gainesville, Fla., and has remained true-to-type since that time.

The new coleus cultivar 'UF15-11-3' has not been observed under all possible environmental conditions. The phenotype of the new cultivar may vary with variations in environment and cultural practices such as temperature, light intensity, fertilization, irrigation, and application of plant growth regulators without any change in genotype.

Plant Breeder's Rights for 'UF15-11-3' have not been applied for. The new coleus cultivar 'UF15-11-3' has not been made publicly available more than one year prior to the filing date of this application.

The new cultivar 'UF15-11-3' was selected because it is the first plant from the program with lance-shaped foliage that is colored orange and chartreuse and with enough vigor to withstand the harsh selection conditions our plants are subjected to in full sun trials in Gainesville, Fla. This combination of traits makes 'UF15-11-3' novel because it has not been observed in the program, and is not currently available in the trade. The new cultivar 'UF15-11-3' is exceptional because it maintains its distinct colors in well-defined zones in shade or sun.

The following are the most outstanding and distinguishing characteristics of the new cultivar 'UF15-11-3' when grown under normal horticultural practices in Gainesville, Fla.:

1. a combination of vigorous, compact growth habit, excellent heat tolerance, and consistent lance-shaped leaves colored orange and chartreuse that are significantly different than other coleus plants;
2. superior stability in foliage color in both sun and shade conditions, maintaining stable color in all conditions;
3. it is a vigorous plant with excellent lateral branching when grown as a stock plant, thus providing ample vegetative propagules for producers; and
4. 'UF15-11-3' has been observed to have long-season performance in landscape trials in Gainesville, Fla.

Plants of the new coleus cultivar 'UF15-11-3' differ from plants of the female parent, 'UF14-2-6', in the following characteristics:

1. 'UF15-11-3' has lance-shaped leaves that are contrasting orange and chartreuse, and pointed at the apex. In contrast, 'UF14-2-6' has smaller leaves colored maroon and lime green that are ovate and not lance-shaped; and
2. 'UF15-11-3' has a robust, well-branched mounded and compact plant form, whereas 'UF14-2-6' is much less vigorous, and has a much more upright plant form with less lateral branching.

Plants of the new coleus cultivar 'UF15-11-3' can be compared to those of 'UF15-6-28' (U.S. Plant Pat. No. 30,970). On the adaxial surface of mature leaves of 'UF15-11-3', the foliage color is bright orange (RHS 178C), with chartreuse-colored leaf margins (RHS N144C). On the adaxial surface of mature leaves of 'UF15-6-28', the foliage color is bright red (RHS 187B) with chartreuse-colored leaf margins (RHS N144C).

DESCRIPTION OF THE FIGURES

The accompanying photographs (as shown in FIGS. 1-3) illustrate the overall appearance of the new coleus cultivar 'UF15-11-3'. The colors shown in these photographs are as true as can be reasonably obtained by conventional photographic procedures. Colors shown in the photographs may differ slightly from the color values cited in the detailed botanical description, which accurately describes the colors of the new coleus cultivar.

FIG. 2 shows the growth habit, form, and foliage of 'UF15-11-3'; and

FIG. 3 shows a close-up of the foliage of 'UF15-11-3'.

DETAILED BOTANICAL DESCRIPTION OF THE CULTIVAR

Figure 1:
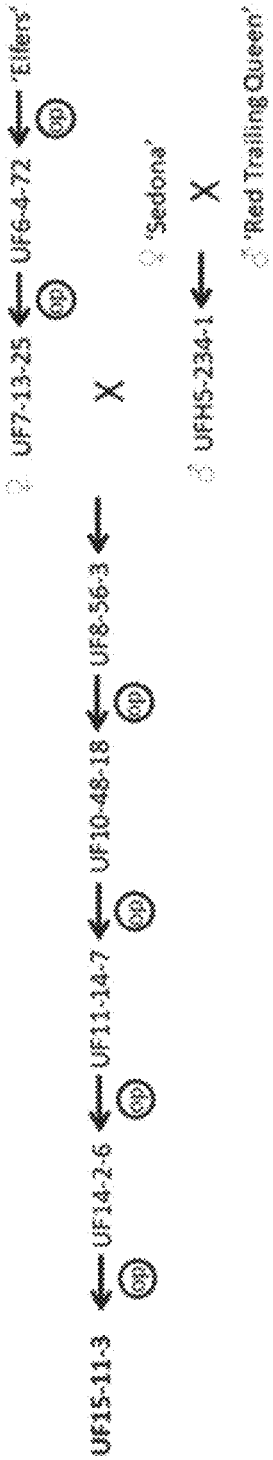
FIG. 1 shows the pedigree of 'UF15-11-3'.
Figure 2:
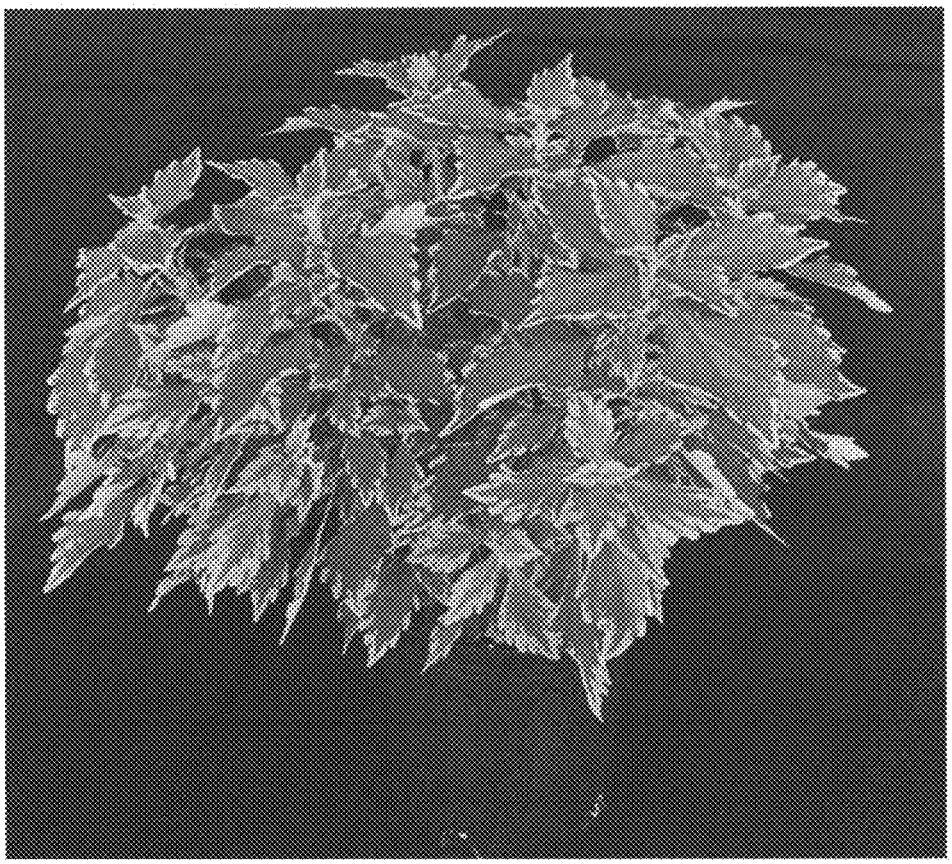
FIGS. 2 and 3 were taken from plants grown nine (9) weeks from unrooted cuttings in June-August 2020 in a glass-covered greenhouse in Gainesville, Fla.
Figure 3:
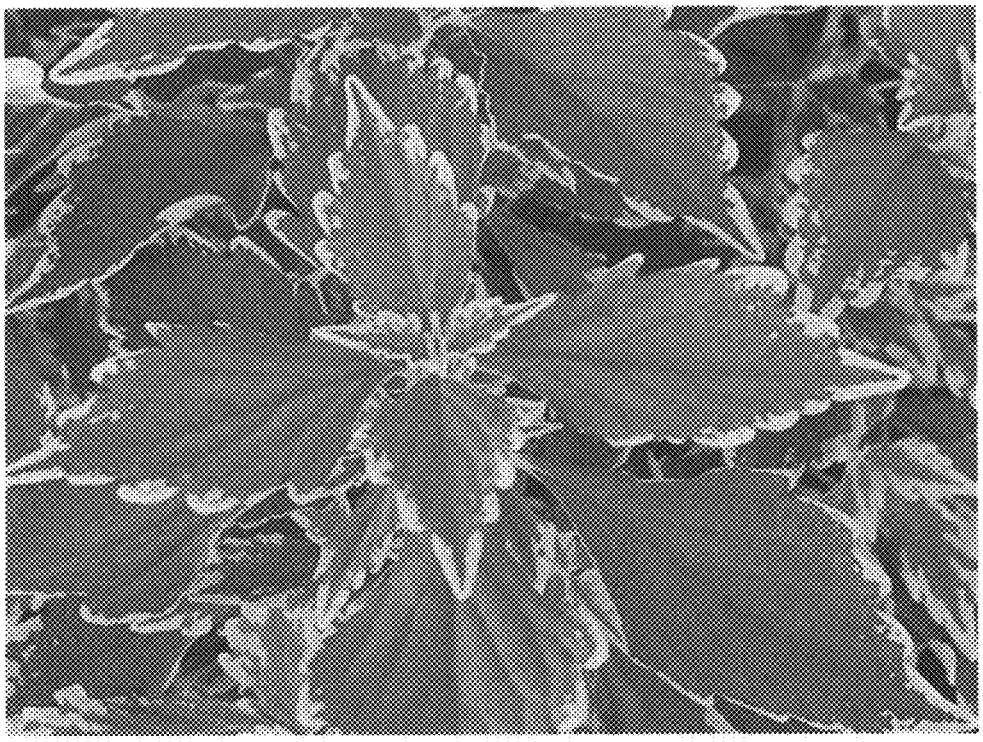

The following detailed description sets forth the distinctive characteristics of the new coleus cultivar 'UF15-11-3'. Color references are to The Royal Horticultural Society of London (R.H.S.) Colour Chart, 2007 (5th Edition).

Description of Growing Conditions

The detailed description was obtained using nine-week-old plants grown from unrooted cuttings in June-August 2020 in a glass-covered greenhouse in Gainesville, Fla. The plants were propagated in mist for ten (10) days after cuttings were stuck, then grown in one-gallon pots for approximately seven and a half additional weeks.

Botanical Description

Botanical classification:
- *Family*.—Lamiaceae.
- *Botanical name*.—*Plectranthus scutellarioides*.
- *Common name*.—Coleus.
- *Cultivar*.—'UF15-11-3'.

Parentage:
- *Female or seed parent*.—'UF14-2-6'.
- *Male or pollen parent*.—Unknown.

Propagation:
- *Type*.—Vegetative meristems having at least one (1) node.
- *Time to initiate roots*.—3-4 days.
- *Time to produce a rooted cutting*.—7-10 days.

Root description:
- *Root description*.—Callus forms in 2-3 days, roots initiate in 3-4 days and become a highly branched cutting in 7-10 days.
- *Rooting habit*.—Fibrous.

Plant description:
- *Plant form*.—Mounded, compact.
- *Growth habit*.—Spreading.
- *Plant height* (*from top of soil*).—25-30 cm.
- *Plant width* (*horizontal plant diameter*).—45-50 cm.
- *Branches*.—Quantity per plant: 9. Branch color: RHS 143B (medium green). Texture: Smooth. Pubescence: Not present. Stem description: Square-shaped stem, 0.6 cm in diameter at the soil line. Branch diameter: 0.4-0.5 cm at the base of a 23 cm long branch. Branch length: 23-25 cm. Internode length: 3-4 cm. Anthocyanin: Not present.

Foliage description:
- *Quantity of leaves per branch*.—24-26.
- *Arrangement*.—Opposite.
- *Fragrance*.—Not fragrant.
- *Length*.—8-10 cm.
- *Width*.—5-6 cm.
- *Shape*.—Ovate. Apex: Broadly acute. Base: Attenuate.
- *Margin*.—Lobed.
- *Leaf texture* (*both surfaces*).—Smooth.
- *Pubescence* (*both surfaces*).—Not present.
- *Color, immature leaf*.—Upper surface, center: RHS 172B (medium brown). Upper surface, margin: RHS N144C (light green). Lower surface: RHS 145A (light green).
- *Color, mature leaf*.—Upper surface, center: RHS 178C (brown red). Upper surface, margin: N144C (light green). Lower surface: RHS 143C (medium green).
- *Venation color*.—Upper surface: RHS 59B (dark purple red). Lower surface: RHS 141C (medium green).
- *Venation pattern*.—Upper surface: Reticulate. Lower surface: Reticulate.
- *Petiole length*.—2-2.5 cm.
- *Petiole diameter*.—0.2 cm.
- *Petiole color*.—RHS 141C (medium green).
- *Petiole texture*.—Smooth, no pubescence.

Flowers and seeds: Flowers and seeds have not been observed to date during formal trials in Gainesville, Fla.

Fruit/seed set: Fruit and seeds have not been observed to date during formal trials in Gainesville, Fla.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Pernonspora lamii*). This pathogen has been observed in stock materials grown closely together in cooler growing seasons.

What is claimed is:

1. A new and distinct *Plectranthus scutellarioides* plant named 'UF15-11-3' as shown and described herein.

* * * * *